United States Patent
Zhao et al.

(10) Patent No.: US 11,253,204 B2
(45) Date of Patent: Feb. 22, 2022

(54) METHOD FOR ASSESSING ELECTROCARDIOGRAM SIGNAL QUALITY

(71) Applicant: Shanghai Lepu CloudMed Co., Ltd, Shanghai (CN)

(72) Inventors: Zifang Zhao, Changping District Beijing (CN); Zhe Li, Beijing (CN); Yue Zhang, Changping District Beijing (CN); Weiwei Zhou, Beijing (CN); Huili Cao, Beijing (CN); Chang Liu, Beijing (CN)

(73) Assignee: Shanghai Lepu CloudMed Co., LTD., Shanghai (CN)

( * ) Notice: Subject to any disclaimer, the term of this patent is extended or adjusted under 35 U.S.C. 154(b) by 22 days.

(21) Appl. No.: 16/624,189

(22) PCT Filed: Jan. 12, 2018

(86) PCT No.: PCT/CN2018/072354
§ 371 (c)(1),
(2) Date: Dec. 18, 2019

(87) PCT Pub. No.: WO2019/100563
PCT Pub. Date: May 31, 2019

(65) Prior Publication Data
US 2020/0107786 A1    Apr. 9, 2020

(30) Foreign Application Priority Data
Nov. 27, 2017  (CN) .......................... 201711203646.X

(51) Int. Cl.
*A61B 5/352*    (2021.01)
*A61B 5/00*    (2006.01)
*A61B 5/366*    (2021.01)

(52) U.S. Cl.
CPC ............ *A61B 5/7221* (2013.01); *A61B 5/352* (2021.01); *A61B 5/366* (2021.01); *A61B 5/7203* (2013.01)

(58) Field of Classification Search
CPC ...... A61B 5/316; A61B 5/7203; A61B 5/7221
See application file for complete search history.

(56) References Cited

U.S. PATENT DOCUMENTS

| 2002/0058878 | A1 | 5/2002 | Kohler et al. |
| 2004/0077941 | A1 | 4/2004 | Reddy et al. |

(Continued)

FOREIGN PATENT DOCUMENTS

| CN | 101449973 B | 9/2010 |
| CN | 104644160 A | 5/2015 |

(Continued)

OTHER PUBLICATIONS

Chinese First Office Action for Chinese Application No. 201711203646 dated Jan. 21, 2020, 7 pages.

(Continued)

*Primary Examiner* — Michael J D'Abreu
(74) *Attorney, Agent, or Firm* — TraskBritt

(57) ABSTRACT

A method for assessing electrocardiogram signal quality, the method comprising: receiving heart beat analysis data by processing electrocardiogram data acquired from an electrocardiogram monitoring device; extracting position information and width information of a QRS complex in the heart beat analysis data; extracting an RR interval signal between two adjacent QRS complex signals; performing QRS complex signal cancellation processing on the RR interval signal to obtain an RR interval signal for which the QRS complex signal is removed; filtering the processed RR interval signal without the QRS complex signal, and performing envelope calculation on the filtered signal to obtain the average power (Continued)

of a noise signal of the RR interval signal for which the QRS complex signal is removed; obtaining a signal quality evaluation index according to the average power of the noise signal and the power of the QRS complex signal.

5 Claims, 1 Drawing Sheet

(56) References Cited

U.S. PATENT DOCUMENTS

| | | | |
|---|---|---|---|
| 2010/0022903 A1 | 1/2010 | Sitzman et al. | |
| 2013/0338519 A1* | 12/2013 | Chen | A61B 5/352 600/521 |
| 2014/0128758 A1 | 5/2014 | Galloway et al. | |

FOREIGN PATENT DOCUMENTS

| | | |
|---|---|---|
| CN | 103431856 B | 9/2015 |
| CN | 105877739 A | 8/2016 |
| CN | 103705214 B | 9/2016 |
| CN | 107224284 A | 10/2017 |
| CN | 105899268 B | 2/2019 |
| CN | 105902263 B | 4/2019 |
| WO | 2013/054242 A1 | 4/2013 |
| WO | 2017/174738 A1 | 10/2017 |

OTHER PUBLICATIONS

Chinese Search Report for Chinese Application No. 201711203646 dated Jan. 0, 2020, 2 pages.
International Search Report for International Application No. PCT/CN2018/072354 dated Sep. 4, 2018, 2 pages.
International Written Opinion for International Application No. PCT/CN2018/072354 dated Sep. 4, 2018, 3 pages.
European Search Report and Search Opinion Received for EP Application No. 18880713, dated Jun. 8, 2021, 5 pages.

* cited by examiner

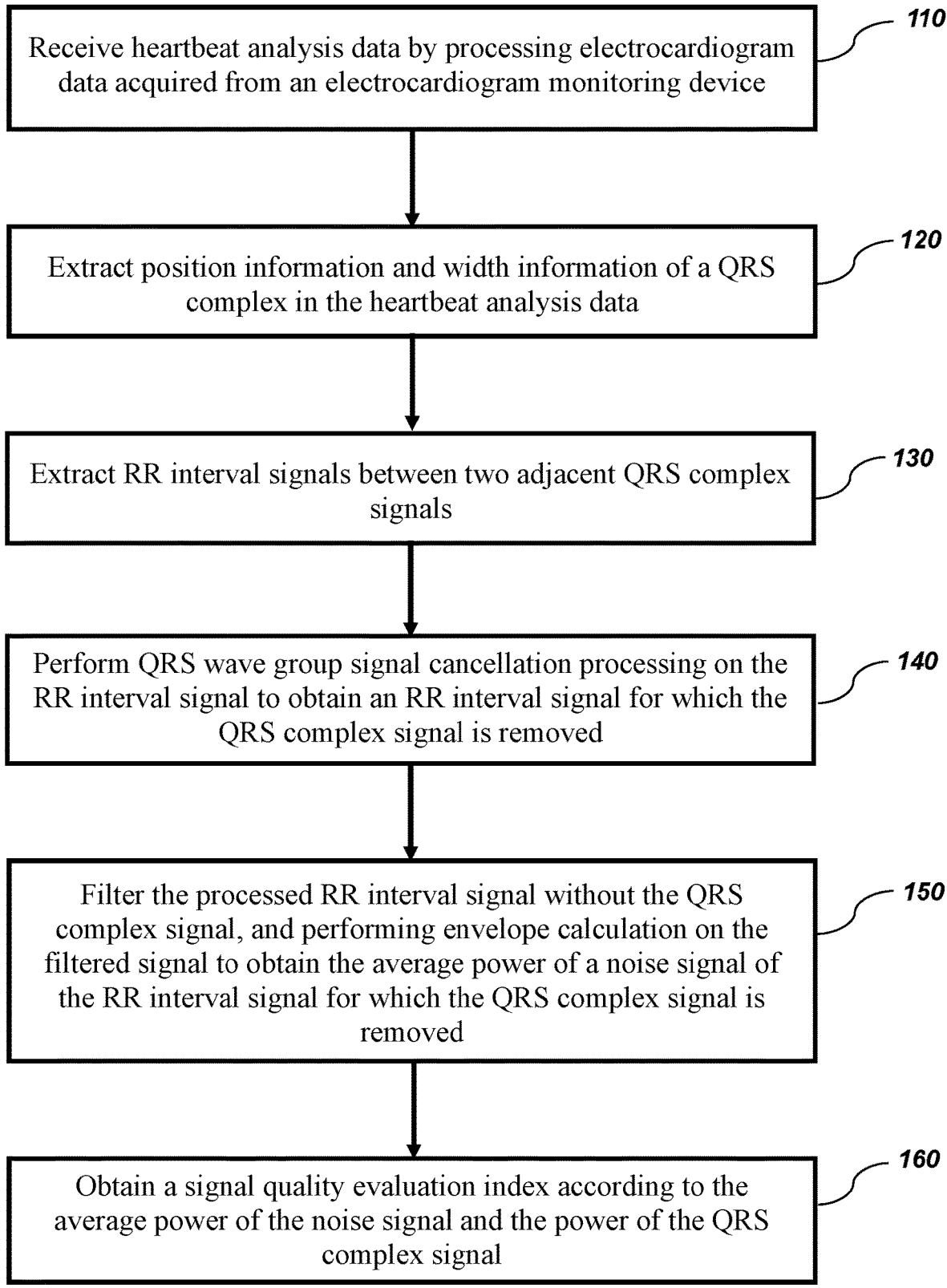

METHOD FOR ASSESSING ELECTROCARDIOGRAM SIGNAL QUALITY

CROSS-REFERENCE TO RELATED APPLICATIONS

This application is a national phase entry under 35 U.S.C. § 371 of International Patent Application PCT/CN2018/072354, filed Jan. 12, 2018, designating the United States of America and published as International Patent Publication WO 2019/100563 A1 on May 31, 2019, which claims the benefit under Article 8 of the Patent Cooperation Treaty to Chinese Patent Application Serial No. 201711203646.X, filed Nov. 27, 2017, entitled "Method for Evaluating Electrocardiogram Signal Quality."

TECHNICAL FIELD

The present disclosure relates to the technical field of signal analysis and, more particularly, to a method for evaluating electrocardiogram signal quality.

BACKGROUND

In 1908, Einthoven began to use electrocardiogram (ECG) to monitor electrophysiological activities of a heart. At present, noninvasive ECG examination has become one of important methods for diagnosis and screening of heart diseases in clinical cardiovascular field. ECG examination can be divided into several categories such as resting ECG, ambulatory ECG and exercise ECG according to clinical application.

ECG is an important measure for observation, diagnosis and treatment of cardiovascular patients, and can monitor whether there is arrhythmia, a frequency of heart beat and the like in real time, and thus, timely and effective measures can be taken according to ECG activities. Although most of ambulatory ECG analysis software in the market can automatically analyze data, in clinical work, a signal quality during ECG detection and recording has a great influence on an accuracy of final output results.

In traditional signal quality evaluation methods, it is generally judged by time characteristics of a QRS sequence and a power spectrum of whole signals. It is difficult to obtain a real estimation in heart beat activities under various pathological states by judging the time characteristics of the QRS sequence. The power spectrum judgment method according to the whole signals is based on frequency characteristics. However, due to an overlap between a frequency spectrum of a large amount of noise and a frequency of a QRS complex signal itself, this judgment method is easily affected by heart rate and pathological QRS waveforms.

BRIEF SUMMARY

The purpose of the present disclosure is to provide a method for assessing electrocardiogram signal quality, so as to provide a basis for judging the electrocardiogram signal quality.

To achieve the above purpose, the present disclosure provides a method for evaluating electrocardiogram signal quality, including:

receiving heart beat analysis data by processing electrocardiogram data acquired from an electrocardiogram monitoring device;

extracting position information and width information of QRS complexes in the heart beat analysis data;

extracting RR interval signals within RR interval between two adjacent QRS complex signals;

performing the process for eliminating QRS complex signal on the RR interval signals to obtain the RR interval signals from which the QRS complex signals are eliminated;

performing filtering processing on the RR interval signals from which the QRS complex signals are eliminated, and performing an envelope calculation on filtered signals to obtain an average power of noise signals in the RR interval from which the QRS complex signals are eliminated; and obtaining a signal quality evaluation index according to the average power of the noise signals and a power of the QRS complex signals.

Preferably, the average power of noise signals in the RR interval signals from which the QRS complex signals are eliminated is an average value of envelope amplitudes of the filtered signals within the RR intervals from which the QRS complex signals are eliminated.

Preferably, the power of the QRS complex signals is a signal power corresponding to a maximum amplitude of the QRS complex signals.

Preferably, the obtaining a signal quality evaluation index according to the average power of the noise signals and a power of the QRS complex signals specifically includes:

calculating, according to the power of the QRS complex signals and the average power of the noise signals, a noise level within the RR interval from which the QRS complex signals are eliminated respect to the QRS complex signals; and taking the noise level as the signal quality evaluation index.

Preferably, the obtaining a signal quality evaluation index according to the average power of the noise signals and a power of the QRS complex signals includes:

calculating the signal quality evaluation index through a formula:

$$SNR(i) = \frac{S_i}{\sum N_{i,t} \div T};$$

where $S_i$ is an amplitude of a i-th QRS complex signal, $N_{i,t}$ is an amplitude of a t-th sample point of the filtered signals in a i-th RR interval from which the QRS complex signals are eliminated, and T is a length of RR intervals from which the QRS complex signals are eliminated.

In the method for evaluating electrocardiogram signal quality according to the embodiments of the present disclosure, through position detection and width judgment of the QRS complex signals, the RR interval signals from which the QRS complex signals are eliminated between two adjacent QRS complex signals are extracted. The frequency bands requiring noise estimation are obtained through the filtering, the envelope is calculated, and the average power is obtained. The electrocardiogram (ECG) signal quality is evaluated according to a power ratio of the noise and QRS complex signals. Through this method, the ECG detection signal quality can be accurately estimated, and an accurate and effective signal quality evaluation can be provided for the ECG automatic analysis.

BRIEF DESCRIPTION OF THE DRAWINGS

FIG. 1 is a schematic diagram illustrating a method for evaluating electrocardiogram signal quality according to an embodiment of the present disclosure.

DETAILED DESCRIPTION

Technical solutions of the present disclosure will be further described in detail below through accompanying drawings and embodiments.

A method for evaluating electrocardiogram signal quality according to an embodiment of the present disclosure provides a manner for accurately evaluating quality of an ECG detection signal.

FIG. 1 is a flowchart illustrating a method for evaluating electrocardiogram signal quality according to an embodiment of the present disclosure. As shown in FIG. 1, the method for evaluating electrocardiogram signal quality of the present disclosure includes the following steps:

Step 110: heart beat analysis data obtained by processing ECG data output by an ECG monitoring device is received.

Specifically, electrical signals are converted into digital signals by the ECG monitoring device for output, which may be single-lead or multi-lead time sequence data. Original data is stored by a data storage and transmission apparatus, and can be transmitted through WIFI, Bluetooth, USB, 3G/4G/5G mobile communication networks, Internet of Things and other means.

Before the ECG signal quality is evaluated, the original data received by transmission needs to be resampled and converted into a preset standard data format by a data format, thereby solving differences in leads, sample frequencies and transmission data formats used by different ECG devices. Converted data in the preset standard data format is processed by digital signal filtering to remove high frequency, low-frequency noise interference and baseline drift, so as to obtain heart beat data. Interference identification is performed on the heart beat data, and the heart beat data is combined to generate the heart beat analysis data according to results of the interference identification, and time rules based on lead parameters of the heart beat data.

Step 120: position information and width information of QRS complexes in the heart beat analysis data are extracted.

Specifically, multiple QRS complex signals included in the heart beat analysis data are obtained through QRS complex detection. Each QRS complex signal corresponds to a heart beat cycle. Then, data identification processing is carried out on each QRS complex signal to determine characteristic points of the QRS complex signals, so as to determine the position information and the width information of the QRS complex signals in time sequence. In addition, a power of each QRS complex signal can also be determined. The power of the QRS complex signals herein is a signal power corresponding to a maximum amplitude of the QRS complex signals.

Step 130: RR interval signals within RR interval between two adjacent QRS complex signals are extracted.

Similarly, according to the characteristic points of the QRS complex signals determined by data identification processing on each QRS complex signal, positions of R waves in the time sequence are determined, and thus the RR interval signals between two adjacent QRS complex signals are obtained.

Step 140: the process for eliminating QRS complex signal is performed on the RR interval signals to obtain RR interval signals from which the QRS complex signals are eliminated.

Signals belonging to QRS complex signals are eliminated from the RR interval signals to obtain RR interval signals other than the QRS complex signals in RR intervals.

Step 150: filtering processing is performed on the RR interval signals from which the QRS complex signals are eliminated, and an envelope calculation is performed on filtered signals to obtain an average power of noise signals in the RR interval from which the QRS complex signals are eliminated.

Specifically, a choice of a filter should avoid an influence of a normal ECG signal itself. Since the evaluation is carried out in a region where there is no QRS complex in the RR intervals from which the QRS complex signals are eliminated, it is only necessary to consider not to overlap with frequency bands of P wave and T wave. Generally, frequencies of the T wave and P wave are lower than 15 Hz, so it is preferable to use a 15 Hz low-pass filter. The structure of the filter is not limited herein, and IIR, FIR or wavelet filters can be selected.

Therefore, the average power of the noise signals in the RR intervals from which the QRS complex signals are eliminated is obtained by calculating an average value of envelope amplitudes of the filtered signals within the RR interval from which the QRS complex signals are eliminated.

Step 160: a signal quality evaluation index is obtained according to the average power of the noise signals and the power of the QRS complex signals.

Specifically, a noise level within the RR interval from which the QRS complex signals are eliminated respect to the QRS complex signals can be calculated according to the power of the QRS complex signals and the average power of the noise signals, and then the noise level is taken as the signal quality evaluation parameter.

The signal quality evaluation index is expressed by a formula:

$$SNR(i) = \frac{S_i}{\sum N_{i,t} \div T};$$

wherein $S_i$ is an amplitude of a i-th QRS complex signal, $N_{i,t}$ is an amplitude of a t-th sample point of the filtered signals in a i-th RR interval from which the QRS complex signals are eliminated, and T is a length of the RR intervals from which the QRS complex signals are eliminated.

The signal quality evaluation index obtained through the above steps can be used for effective data screening of ECG monitoring data in ECG automatic analysis process, and for selection and evaluation of typical data segments of ECG events.

In a method for evaluating electrocardiogram signal quality according to the embodiments of the present disclosure, through position detection and width judgment of the QRS complex signals, the RR interval signals from which the QRS complex signals are eliminated between two adjacent QRS complex signals are extracted. The frequency bands requiring noise estimation are obtained through the filtering, the envelope is calculated, and the average power is obtained. The ECG signal quality is evaluated according to a power ratio of the noise and QRS complex signals. Through this method, the ECG detection signal quality can be accurately estimated, and an accurate and effective signal quality evaluation can be provided for the ECG automatic analysis.

Those skilled in the art should further realize that the units and algorithm steps of the examples described in the embodiments disclosed herein can be implemented in electronic hardware, computer software, or a combination of the two. In order to clearly illustrate the interchangeability of hardware and software, the composition and steps of each example have been generally described according to functions in the above description. Whether these functions are implemented in hardware or software depends on the specific application and design constraints of the technical solutions. Those skilled in the art may use different methods to implement the described functions for each specific application, but such implementation should not be considered to be beyond the scope of the present disclosure.

The steps of methods or algorithm described in the embodiments disclosed herein may be implemented in hardware, a software module executed by a processor, or a combination of the two. The software module may be placed in random access memory (RAM), memory, read only memory (ROM), electrically programmable ROM, electrically erasable programmable ROM, registers, hard disks, removable disks, CD-ROM, or any other form of storage medium known in the technical field.

The specific embodiments described above have further explained the purpose, technical solution and beneficial effects of the present disclosure in detail. It should be understood that the above is only specific embodiments of the present disclosure and is not used to limit the scope of protection of the present disclosure. Any modification, equivalent substitution, improvement, etc., made within the spirit and principles of the present disclosure should be included in the scope of protection of the present disclosure.

What is claimed is:

1. A method for evaluating electrocardiogram signal quality, comprising:
    receiving heart beat analysis data by processing electrocardiogram data acquired from an electrocardiogram monitoring device;
    extracting position information and width information of QRS complexes in the heart beat analysis data;
    extracting RR interval signals within RR interval between two adjacent QRS complex signals;
    performing a process for eliminating QRS complex signal on the RR interval signals to obtain the RR interval signals from which the QRS complex signals are eliminated;
    performing filtering processing on the RR interval signals from which the QRS complex signals are eliminated, and performing an envelope calculation on filtered signals to obtain an average power of noise signals in the RR interval from which the QRS complex signals are eliminated; and
    obtaining a signal quality evaluation index according to the average power of noise signals and a power of the QRS complex signals, which comprises:
        calculating the signal quality evaluation index through a formula:

$$SNR(i) = \frac{S_i}{\sum N_{i,t} \div T};$$

wherein $S_i$ is an amplitude of a i-th QRS complex signal, $N_{i,t}$ is an amplitude of a t-th sample point of the filtered signals in a i-th RR interval from which the QRS complex signals are eliminated, and T is a length of RR intervals from which the QRS complex signals are eliminated.

2. The method for evaluating electrocardiogram signal quality according to claim 1, wherein the average power of noise signals in the RR interval signals from which the QRS complex signals are eliminated is an average value of envelope amplitudes of the filtered signals within the RR interval from which the QRS complex signals are eliminated.

3. The method for evaluating electrocardiogram signal quality according to claim 1, wherein the power of the QRS complex signals is a signal power corresponding to a maximum amplitude of the QRS complex signals.

4. The method for evaluating electrocardiogram signal quality according to claim 1, wherein the obtaining a signal quality evaluation index according to the average power of noise signals and a power of the QRS complex signals comprises:
    calculating, according to the power of the QRS complex signals and the average power of noise signals, a noise level within the RR interval from which the QRS complex signals are eliminated respect to the QRS complex signals; and
    taking the noise level as the signal quality evaluation index.

5. The method for evaluating electrocardiogram signal quality according to claim 4, wherein the obtaining a signal quality evaluation parameter according to the average power of the noise signals and a power of the QRS complex signals comprises:
    calculating the signal quality evaluation parameter through the formula:

$$SNR(i) = \frac{S_i}{\sum N_{i,t} \div T};$$

wherein $S_i$ is the amplitude of the i-th QRS complex signal, $N_{i,t}$ is the amplitude of the t-th sample point of the filtered signals in the i-th RR interval from which the QRS complex signals are eliminated, and T is the length of RR intervals from which the QRS complex signals are eliminated.

* * * * *